(12) United States Patent
Ivarsson

(10) Patent No.: US 7,012,694 B2
(45) Date of Patent: *Mar. 14, 2006

(54) APPARATUS AND METHOD FOR TOTAL INTERNAL REFLECTION SPECTROSCOPY

(75) Inventor: Bengt Ivarsson, Bälinge (SE)

(73) Assignee: Biacore AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/869,824

(22) Filed: Jun. 16, 2004

(65) Prior Publication Data

US 2005/0062974 A1    Mar. 24, 2005

Related U.S. Application Data

(63) Continuation of application No. 10/098,740, filed on Mar. 14, 2002, now Pat. No. 6,775,003.

(60) Provisional application No. 60/276,637, filed on Mar. 16, 2001.

(51) Int. Cl.
    *G01N 21/55*    (2006.01)
(52) U.S. Cl. ..................... 356/445; 436/518
(58) Field of Classification Search .............. 356/445; 422/82.05; 436/518
    See application file for complete search history.

(56) References Cited

U.S. PATENT DOCUMENTS

| | | | |
|---|---|---|---|
| 5,023,053 A | * | 6/1991 | Finlan ................. 422/82.05 |
| 5,341,215 A | * | 8/1994 | Seher .................... 356/445 |
| 5,416,573 A | * | 5/1995 | Sartor, Jr. ............... 356/71 |
| 5,583,643 A | * | 12/1996 | Gass et al. .............. 356/445 |
| 5,912,181 A | | 6/1999 | Petcavich |
| 5,922,594 A | | 7/1999 | Lofas |

(Continued)

FOREIGN PATENT DOCUMENTS

JP        04-15976         1/1992

(Continued)

OTHER PUBLICATIONS

R.D. Harris and J.S. Wilkinson, Waveguide Surface Plasmon Resonance Sensors, University of Southampton 1994.

(Continued)

*Primary Examiner*—Richard A. Rosenberger
(74) *Attorney, Agent, or Firm*—Seed IP Law Group PLLC

(57)    ABSTRACT

An optical apparatus for total internal reflection spectroscopy comprises: a transparent body having an internally reflective surface; at least one source of electromagnetic radiation for providing at least one beam of collimated electromagnetic radiation; optical scanning means for directing the beam or beams to the transparent body so that the radiation is internally reflected at the reflective surface, and sequentially or continuously scanning the incident angle of the radiation over an angular range; at least one detector for detecting electromagnetic radiation exiting the transparent body, and means for counteracting variation of the irradiance in the illuminated area of the surface during the angular scan, or the effect of such variation on the reflected beam or beams. An optical apparatus for examining thin layer structures on a surface for differences in respect of optical thickness and/or refractive index, and a method for total internal reflection spectroscopy are also disclosed.

16 Claims, 5 Drawing Sheets

U.S. PATENT DOCUMENTS

| | | | |
|---|---|---|---|
| 5,955,729 A | 9/1999 | Nelson et al. | |
| 5,965,456 A | 10/1999 | Malmqvist et al. | |
| 5,972,612 A | 10/1999 | Malmqvist et al. | |
| 6,008,893 A | 12/1999 | Roos et al. | |
| 6,127,183 A | 10/2000 | Ivarsson et al. | |
| 6,143,513 A | 11/2000 | Lofas | |
| 6,143,574 A | 11/2000 | Karlsson et al. | |
| 6,200,814 B1 | 3/2001 | Malmqvist et al. | |
| 6,207,381 B1 | 3/2001 | Larsson et al. | |
| 6,289,286 B1 | 9/2001 | Andersson et al. | |
| 6,330,062 B1 | 12/2001 | Corn et al. | |
| 6,407,804 B1 * | 6/2002 | Hillmann et al. | 356/71 |
| 6,417,924 B1 | 7/2002 | Kimura | |
| 6,417,925 B1 | 7/2002 | Naya | |
| 6,421,128 B1 | 7/2002 | Salamon et al. | |
| 6,424,418 B1 | 7/2002 | Kawabata et al. | |
| 6,493,097 B1 * | 12/2002 | Ivarsson | 356/630 |
| 6,775,003 B1 * | 8/2004 | Ivarsson | 356/445 |

FOREIGN PATENT DOCUMENTS

| | | |
|---|---|---|
| JP | 2001-188023 | 7/2001 |
| JP | 2001-255267 | 9/2001 |
| WO | WO 92/05426 | 4/1992 |
| WO | WO 94/25850 | 11/1994 |
| WO | WO 98/22808 | 5/1998 |
| WO | WO 98/34098 | 8/1998 |

OTHER PUBLICATIONS

Abstract of JP 04-15976, Patent Abstracts of Japan, Jan. 21, 1992.

Abstract of JP 2001-188023, Patent Abstracts of Japan, Jul. 10, 2001.

Abstract of JP 2001-255267, Patent Abstracts of Japan, Sep. 21, 2001.

* cited by examiner

APPARATUS AND METHOD FOR TOTAL INTERNAL REFLECTION SPECTROSCOPY

CROSS-REFERENCES TO RELATED APPLICATIONS

This application is a continuation of U.S. patent application Ser. No. 10/098,740, filed Mar. 14, 2002, now U.S. Pat. No. 6,775,003, which claims the benefit of U.S. Provisional Application No. 60/276,637 filed Mar. 16, 2001 and also claims priority to Swedish Application No. 0100889-5 filed Mar. 14, 2001; each of which is incorporated herein by reference in its entirety.

BACKGROUND OF THE INVENTION

1. Field of the Invention

The present invention relates to improvements in total internal reflection (TIR) spectroscopy, and more particularly to an apparatus and method for TIR-based spectroscopic imaging with improved angular scanning, particularly attenuated total reflection (ATR) imaging spectroscopy and microscopy.

2. Description of the Related Art

Attenuated total reflection (ATR) spectroscopy, also known as internal reflection spectroscopy (IRS), originates in the observation by Newton almost two centuries ago that a propagating wave of radiation which undergoes total internal reflection (TIR) in a higher index of refraction medium in contact with a lower index of refraction medium gives rise to an evanescent field in the lower refractive index medium. It was, however, not until 1960 that this phenomenon was exploited for producing absorption spectra. Since then, numerous ATR-based applications have been developed, many of them in the biosensor field. In biosensors based on ATR, the evanescent field probes a thin layer (penetration depth about one wavelength) of sample-containing material at a solid/liquid interface, resulting in a measurable attenuation of the reflected radiation in proportion to the imaginary part of the refractive index of the thin layer, i.e., absorption spectroscopy.

As is well-known, the spectrum in ATR-spectroscopy consists of a reflectance vs. wavelength curve or spectrum, where the angle of incidence may be scanned in order to vary evanescent wave penetration depth (see e.g., Harrick, N. J., Internal Reflection Spectroscopy, Harrick Scientific Corp., New York, 1967; and Mirabella, F. M. Jr., Internal Reflection Spectroscopy: Review and Supplement, Harrick Scientific Corp., New York, 1985). Photon absorbance at the ATR-sensor surface, with or without evanescent electrical field strength enhancing metal film or particles, is detected as a more or less sharp and deep minimum, or dip, in the internal reflectance (TIR) curve, and the depth (absorbance peak) is a measure of the amount of detected sample, and the wavelength is used to identify the kind of molecule.

A variant of ATR-spectroscopy, hereinafter referred to as SPR-spectroscopy, is based on surface plasmon resonance (SPR) in an electrical field-strengthening layer of metal film or metal islands or particles applied on the solid medium at the solid/liquid interface. The angle (or wavelength) corresponding to the minimum or centroid of the photon absorbance peak, or reflectance dip, and/or the change in angle, is a measure of the amount of detected sample. More particularly, the change in SPR-angle and/or SPR-wavelength is a measure of the change in the real part of the refractive index (n) and/or the change in the thickness (d) of the sample interaction layer or layers at the solid/liquid interface. If the sample also allows photon absorbance, this can be measured via changes in the shape (reflectance minimum and dip width) of the SPR-ATR-curve.

The surface concentration of the sample can be calculated from the shift in SPR-angle and/or SPR-wavelength by use of well-known relations between surface concentration and layer structural parameters n, d, and empirical or calculated refractive index increment of the sample solute (De Feijter, J. A., et al., *Biopolymers* 17:1759, (1978); and Salaman, Z., et al., *Biochemistry* 33:13706, (1994)).

In some SPR-spectroscopic optic configurations, e.g., using both p- and s-polarized light, the photon absorbance is converted into a peak rather than a dip in the reflectance curve, and the angle (or wavelength) position, or shift in position, for this peak is used as a quantitative measure of the amount, or change in amount, of detected sample.

SPR-based sensors are commercially available for use in research and development, for example the BIACORE® instrument line from Biacore AB, Uppsala, Sweden. These instruments use a sensor glass chip covered with a thin gold film and an integrated fluid cartridge for passing sample fluid and other fluids over the sensor chip. A fan shaped beam of light is coupled to the sensor chip via a prism such that an angular range of incident light is reflected internally along a line at the glass/gold film interface creating a plasmon evanescent field at the gold film/fluid interface, and the reflected light intensity distribution versus angle of incidence for a row of sensor spots along the illuminated line, is detected by a photodetector array.

The sensitivity in the detectable change of the angle (or wavelength) at the dip or peak (or in some cases, dips or peaks) of the SPR spectrum is mainly limited by the degree of constancy, drift and noise of the background light intensity of the TIR-curve. Ideally, the TIR-curve is constant versus angle. In practice, however, due to variation of reflectance with the angle of incidence, and the radiation distribution from the light source, the TIR-curve will generally be a gaussian type curving line with at least one maximum and which at its low and high angle ends, respectively, is more or less sloping. The sensitivity of SPR-spectroscopy is, of course, particularly in the case of kinetic studies (measurement of the time dependence of the reflectance curve, shape and/or position), higher the more stable the light intensity at total internal reflection is over the angular or wavelength range of interest, i.e., the less dependent the "background" TIR-curve is on the angle (or wavelength).

The sensitivity of SPR-spectroscopy can thus be further increased if the TIR-curve is normalized, such as by a computer software algorithm. This usually requires highly stable TIR-curve data, i.e., low temporal noise and drift, and that the TIR-curve has as little curvature and sloping as possible and is as smooth as possible. Such computerized normalization of the TIR-curve is, for example, done in the BIACORE® instruments mentioned above, where the normalization procedure is performed on the TIR-spectrum with a sample of refractive index high enough to give TIR for the angle range used. Due to the use of a focused light beam (spot or line) and a static optical system in the present BIACORE® instruments, the illuminated sensor surface for TIR is fixed (stationary). The stability of the provided irradiance is therefore only limited by noise and drift in the light source.

Whereas conventional ATR-spectroscopy measures the surface characteristics of a sample at a fixed small spot or a thin line, spatial scanning of the incident light beam across a surface area may produce an image of the spectral property distribution over the scanned area. This technique is usually referred to as ATR-microscopy. Thus, for instance, various arrangements for surface plasmon microscopy (SPM) have been proposed for detection of the spatial distribution of the refractive index. Rather than spatially scanning a focused line or light beam across the sensor surface area with time, it has also been described to momentarily illuminate and image the whole surface area in question and scan the incident light angle or wavelength with time. A biosensor based on ATR-microscopy may, for example, be used for analyzing a large number, or an array, of sample spots simultaneously.

An example of an ATR-sensor apparatus of the last-mentioned type based on scanning the angle of incidence of a probing collimated (parallel) beam which illuminates the whole surface area is disclosed in WO 98/34098 (the full disclosure of which is incorporated by reference herein). A representative illustration of this system is given in FIG. 1 herein, where a light source, LS, illuminates a collimator optics, CO, to produce a parallel light beam. The beam passes an interference filter, I, as a monochromatic beam and impinges on a first flat scanner mirror, SM1, to be deflected onto a second scanning mirror, SM2. The latter deflects the beam into a prism Pr for coupling the light into a sensor surface, SS, the beam being totally internally reflected at the sensor interface side of the coupling prism. The p-polarized component of the beam then passes a polarizer, P, whereupon the beam is directed into a spherical objective, SO, to produce a real image on a photo detector array or matrix, D, of the sensor surface area from its reflected light intensity pattern.

The detector array D is arranged such that the real image of the sensor area is produced on a rectangular part, D, of the array, the objective SO having its real image plane positioned at the plane of the photodetector array. Numerals 1, 2 and 3 at the detector array D denote the respective images of the corresponding subzones on the sensor surface SS, indicated at 1', 2' and 3', respectively.

The two scanning mirrors SM1 and SM2 have a related rotational or oscillating movement to produce an angularly scanned collimated beam incident within a range of angles of incidence on the sensor surface side of the prism Pr. "Beam walking" of the illuminated area, which is caused by refraction of the collimated light at the entrance of the prism Pr during the scan of the angle of entrance and would give an irregular irradiance (radiant power per unit area) at the sensor surface, is avoided by synchronizing the movements of the scanning mirrors SM1 and SM2 (as well as adapting the distances and angles between mirrors and prism, and scanned angular range of the mirrors) to provide a fixed center for the intersection of the incident collimated light beam with the sensor surface SS.

In the general type of ATR-microscope described above, the momentary incident angle of the collimated light beam irradiating the sensor surface during the angle scan may de determined by various means. WO 98/34098 proposes to determine the momentary incident angle by detecting a part of the light beam reflected at the sensor surface on a second detector. More particularly, the objective SO comprises an additional part having its back focal plane positioned at the plane of the photodetector array to permit a minor part of the reflected collimated beam to be focused onto a minor, linear part of the detector area so that each angle of reflection corresponds to a specific linear detector position within the detector area.

While in the ATR-microscope described in WO 98/34098 the fixed center of the illuminated area thus gives a more stable irradiance, or optical power distribution across the cross-section of the beam at the sensor surface than in the case of beam walking, this ATR-microscope has another shortcoming.

Thus, in WO 98/34098, as in conventional ATR-spectroscopy, the center angle of the collimated beam is orthogonally incident onto the entrance surface of the ATR-prism. During the angle scan of this collimated beam, however, the angle of incidence at the entrance surface of the prism will be oblique, a typical angle range being, say, 15°. Therefore, even for an illuminated ATR-sensor area with eliminated beam walking, i.e., a fixed center during angle scan, there will be a variation in the light intensity, or irradiance, with the angle of incidence since the intersection area of the incident collimated beam (of mainly constant beam cross-section area) with the ATR-surface will vary in accordance to Lambert's Cosine Law. The length of the intersection area thus has a fixed center but the length may be said to "oscillate" around its center.

For example, if the length of the intersection area is denoted L, the length L=(beam diameter)/cosine(angle of incidence), or, in case of a rectangular beam cross section, L=(beam cross-section length)/cosine(angle of incidence). This causes, even if the beam walking has been eliminated, L (and the illuminated area) to increase, and the irradiance to decrease, the larger the angle of incidence at the sensor area. The irradiance is proportional to cosine(angle of incidence), during the angle scan by the following exemplary factors: for angle of incidence scan 63° to 77°: 2.0×; for angle of incidence scan 62° to 82°: 3.37×; and for angle of incidence scan 64° to 84°: 4.19×.

This monotone continuously decreasing light intensity with cosine(angle of incidence) creates a correspondingly sloping TIR-data vs. angle curve. As is readily seen, the reflectance at 77° will be about 50% of that at 63°, and at 84° only about 25% of that at 63°.

Such a substantial decrease in light intensity with increased angle of incidence can not readily be compensated for by computerized data processing like the above-mentioned normalization of the TIR-curve, or at least not without a complex normalization method and software. There is therefore a need for means that overcome the problem of varying light intensity during angular scan in ATR-based microscopy.

Related to ATR-microscopy are other microscopic techniques also based on the evanescent wave phenomenon at total internal reflection without or with evanescent field enhancing metal films or textures, such as, for example, total internal reflection fluorescence (TIRF), total internal reflection phosphorescence, and scattered total internal reflectance (STIR). To overcome the above-mentioned problem of varying light intensity during angular scan would therefore be valuable also in those as well as in other related TIR-techniques.

BRIEF SUMMARY OF THE INVENTION

The present invention overcomes the disadvantages of the prior art TIR-based microscopes, such as the ATR-microscope, and offers additional advantages. In brief, the present invention is based on the concept of varying the intensity of the collimated beam incident on a TIR-sensor surface of fixed center position (i.e., eliminated beam walking) with the angle of incidence, such that lengthwise extension of the illuminated sensor surface area as the angle of incidence is increased, or the effect of such length extension, is counteracted. In this way, the variation of the radiation intensity at the TIR-sensor surface of fixed center position during angular scan may thus be eliminated or at least considerably reduced.

In one aspect, the present invention therefore provides an optical apparatus for total internal reflection (TIR) spectroscopy comprising:

a transparent body having a first entrance surface for incident electromagnetic radiation, a second plane internally reflective surface for reflecting radiation transmitted from the first surface through the transparent body, and a third exit surface through which electromagnetic radiation reflected at the second surface exits the transparent body, at least one source of electromagnetic radiation, collimating means for collimating radiation emitted from the at least one source of electromagnetic radiation to at least one beam of collimated electromagnetic radiation, optical scanning means, arranged between the collimating means and the transparent body, for directing at least part of the collimated electromagnetic radiation to the transparent body so that the radiation is internally reflected at the second surface, and sequentially or continuously scanning the incident angle of the radiation at the second surface over an angular range, the illuminated area or areas having an at least substantially fixed center position, and at least one detector for detecting electromagnetic radiation exiting from the transparent body.

The apparatus is characterized in that it comprises means for varying the cross-sectional intensity of at least one of (i) the at least one beam of collimated electromagnetic radiation incident on the second plane surface of the transparent body and (ii) the at least one beam of collimated electromagnetic radiation reflected from the second plane surface of the transparent body, in dependence of the incident angle at the second surface during the angular scan, so that variation of the irradiance at the illuminated area or areas of fixed center position of the second plane surface due to varying length extension in the plane of incidence of the illuminated area or areas during the angular scan, or the effect of such variation on the reflected beam or beams, is counteracted.

In one embodiment of the above-mentioned aspect of the present invention, the apparatus is to be used for attenuated total reflection (ATR) spectroscopy and the detector or detectors are arranged to detect electromagnetic radiation totally internally reflected at the second surface and exiting from the third surface of the transparent body.

In another embodiment, the detector or detectors are arranged to detect electromagnetic radiation originating from evanescent wave stimulated fluorescence or phosphorescence of a substance(s) in contact with the second reflective surface of the transparent body.

In still another embodiment, the detector or detectors are arranged to detect electromagnetic radiation originating from scattering of a substance(s) at the second surface of the transparent body.

In yet another embodiment, the detector or detectors are arranged to detect at least two of electromagnetic radiation totally internally reflected at the second surface, electromagnetic radiation originating from evanescent wave stimulated fluorescence or phosphorescence, and electromagnetic radiation originating from scattering at the second surface of the transparent body.

The above mentioned entrance and exit surfaces of the transparent body may optionally be one and the same surface.

In another aspect, the present invention provides an optical apparatus for examining thin layer structures on a surface for differences in respect of optical thickness (and/or refractive index), comprising:

a sensor unit having at least one sensing surface with a number of zones capable of exhibiting thin layer structures of varying optical thickness, particularly as the result of contact with a sample, at least one source of electromagnetic radiation, collimating means for collimating radiation emitted from the at least one source of electromagnetic radiation to at least one beam of collimated electromagnetic radiation, optical means for coupling at least part of the collimated electromagnetic radiation to the sensor unit to illuminate a sensing surface area or areas thereof, detector means, means for imaging onto the detector means at least one of (i) radiation internally reflected from the illuminated sensing surface area or areas, (ii) radiation originating from sample on the sensing surface through evanescent wave stimulated fluorescence or phosphorescence, and (iii) radiation originating from scattering from sample at the sensing surface, for detecting the intensities of the radiation reflected or originating, respectively, from the different parts of the illuminated area or areas, means for sequentially or continuously scanning the radiation incident at the optical coupling means and at the illuminated area or areas of the at least one sensing surface over a range of incident angles, the illuminated area or areas having an at least substantially fixed center position, means for determining each angle of incidence of electromagnetic radiation impinging on the at least one sensing surface, and evaluation means for determining from the relationship between detected intensity of radiation imaged on the detector means and incident angle of the radiation reflected at the sensing surface or surfaces, the optical thickness of each sensing surface zone to thereby produce a (morphometric) image of the optical thickness of the at least one sensing surface.

The apparatus is characterized in that it comprises means for varying the cross-sectional intensity of at least one of (i) the at least one beam of collimated electromagnetic radiation incident on the at least one sensing surface area of the sensor unit, and (ii) the at least one beam of collimated electromagnetic radiation reflected from the at least one sensing surface area, in dependence of the incident angle at the sensing surface or surfaces during the angular scan, so that the variation of the irradiance in the illuminated area or areas of fixed center position of the sensing surface or surfaces due to varying length extension in the plane of incidence of the illuminated area or areas during the angular scan, or the effect of such variation on the reflected beam or beams, is counteracted.

In still another aspect, the present invention provides a method of performing total internal reflection based spectroscopy, which method comprises:

irradiating at least one area of a plane surface of a transparent body with at least one collimated beam of electromagnetic radiation so that the radiation is totally internally reflected at the surface, imaging onto a respective two-dimensional detector array at least one of (i) radiation internally reflected from the illuminated area or areas, (ii) fluorescent or phosphorescent radiation from the illuminated area or areas caused by evanescent wave stimulation, and (iii) radiation originating from evanescent wave stimulated scattering at the illuminated area or areas, sequentially or continuously scanning the incident angle over an angular range, the illuminated area or areas having an at least substantially fixed center position during angular scan, measuring at at least a number of incident angles of the radiation reflected at the plane surface of the transparent body, the intensities of the radiation imaged on different parts of the detector array (D), and determining from the detected radiation intensities at the different incident angles at the transparent body surface, at least one of an optical thickness image, a refractive index image, a surface concentration image of the surface, and the variation of such images with time.

The method is characterized in that it comprises continuously varying the cross-sectional intensity of at least one of (i) the at least one beam of collimated electromagnetic radiation incident on the plane surface of the transparent body, and (ii) the at least one beam of collimated electromagnetic radiation reflected from the plane surface of the transparent body, in dependence of the incident angle at the surface during the angular scan to reduce variations of the intensity of radiation in the illuminated area or areas of fixed center position of the surface due to varying length extension in the plane of incidence of the illuminated surface area or areas of fixed center position during the angular scan, or the effect of such variation with time on the reflected beam or beams.

In one embodiment, the method is used for kinetic studies of binding events at a sensor surface.

In a particular embodiment of the above method aspect of the invention, ATR-spectroscopy is performed, i.e., the radiation internally reflected from the illuminated area or areas is imaged onto the detector array.

In preferred embodiments of the above apparatus and method aspects of the invention, variations of the intensity of radiation in the illuminated area(s) of the surface of the transparent body caused by varying length extension of the illuminated area(s) during the angular scan are counteracted by varying the length extension in the plane of incidence of the incident beam (or beams) of collimated electromagnetic radiation in dependence of the incident angle during the angular scan, and more particularly such that the beam cross sectional area is decreased as the angle of incidence at the surface is increased.

Optionally, the apparatuses and method, respectively, of the present invention are arranged to permit use of at least two different wavelengths.

The above and other aspects of the invention will be evident upon reference to the attached drawings and the following detailed description.

DETAILED DESCRIPTION OF THE INVENTION

Figure 1:
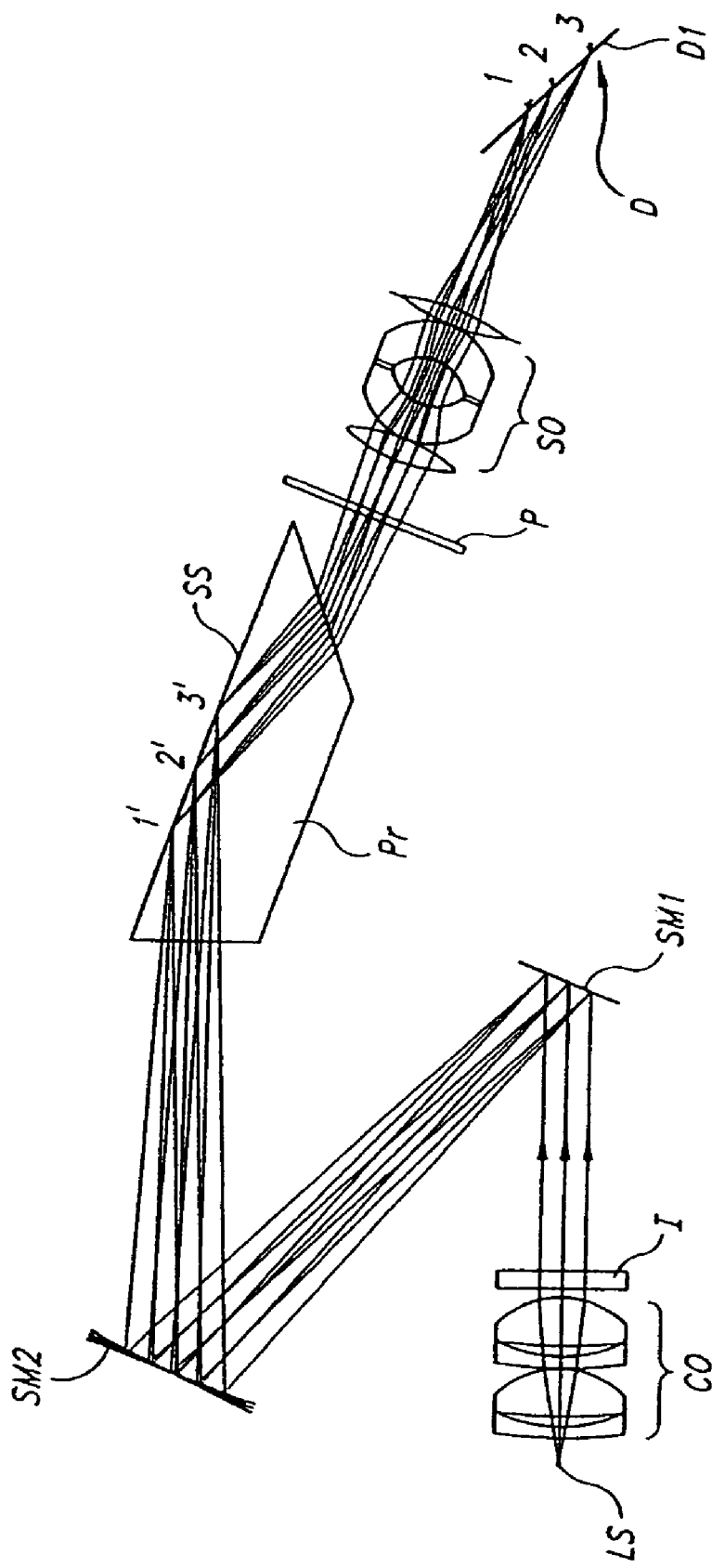
FIG. 1 is a schematic sectional view of a prior art ATR-microscopy system.

U.S. patents, U.S. patent application publications, U.S. patent applications, foreign patents, foreign patent applications and non-patent publications referred to in this specification and/or listed in the Application Data Sheet, are incorporated herein by reference, in their entirety.

As mentioned above, the present invention is directed to overcoming in TIR-based microscopy, such as ATR-microscopy, the problem of varying irradiance at an internally reflective surface, such as that of an ATR-prism, when irradiating the surface with collimated electromagnetic radiation (with or without beam-walking) and scanning the angle of incidence over an angular range. As already set out, the variation in irradiance is due to the beam intersection increasing as the angle of incidence increases at the beam-intersected internally reflective surface.

According to the invention, this problem is solved by providing means for counteracting the undesired variation in radiation intensity at the internally reflective surface with the angle of incidence to provide for a substantially constant radiation intensity of the incident collimated beam in the plane of the internally reflective surface during the angle scan, or, alternatively, counteracting the effect of such variation on the reflected beam. This may be achieved by either (i) for a beam of constant optical power, continually decreasing the cross-section dimension of the beam (or beam diameter for a circular beam) incident at the internally reflective surface as the angle of incidence at the reflective surface is increased; (ii) for a beam of variable optical power, continually increasing the intensity of the (incident or reflected) beam of electromagnetic radiation as the angle of incidence at the reflective surface is increased; or (iii) using a combination of variants (i) and (ii).

It is also within the scope of the present invention to reduce the effect of such undesired variation of the irradiance at the reflective surface by affecting or modifying the detector response, such as, e.g., modifying the response signal from the detector, optionally in combination with one or more of the approaches (i) and (ii) above.

Some of the technical terms and expressions used in this specification and the appended claims will be defined below or are as defined in the above-mentioned WO 98/34098 (the disclosure of which is incorporated herein by reference in its entirety). Otherwise, the technical terms and expressions have the same meaning as commonly understood to one of ordinary skill in the art to which this invention belongs.

The term "electromagnetic radiation" as used herein means radiation in the visible region (from about 400 to about 750 nm) and in the infrared region (from about 750 nm to about 20 $\mu$m), i.e,. in the wavelength range from about 0.4 $\mu$m to about 20 $\mu$m. For simplicity, it will in the following description be referred to as "light".

The "source of electromagnetic radiation" may, for example, be a light emitting diode (LED), laser diode, or an array or bar of LED's or laser diodes. For simplicity, it will hereinafter be referred to as "light source".

The "transparent body" may be an integral element or consist of two (or optionally more) separate elements in optical light-coupling contact with each other. The transparent body containing the internally reflective surface will below often be referred to as transparent ATR-body, or simply ATR-body or ATR-prism, and for simplicity also in total internal reflection contexts not restricted to ATR.

The term "optical thickness" as used herein defines a composite optical property of a material which is a function of both its physical thickness and its refractive index (the complex index of refraction (ñ) consists of a real part (n) responsible for beam refraction, and an imaginary part (k) responsible for the absorption, or beam attenuation, in the medium, i.e., ñ=n−ik).

Morphometric images of the optical thickness, as obtainable by the present invention, may reflect a change in refractive index and/or physical thickness.

The internally reflective surface supports the thin layer of matter to be probed by the evanescent wave elicited by total internal reflection (such as in ATR) and will below often be referred to as a sensor surface.

As is well known, there are two common ways of coupling the light to the sensor surface for creation of an evanescent wave, either by a prism or by a grating. As is also well known, in the prism-coupling case, the sensor surface may be a surface of the prism or that of a separate sensor element, such as a glass or plastic plate, in optical light-coupling contact with the prism, such as via a refractive index matching medium. In the latter case, the "internally reflective surface" will be a surface of this separate sensor element. In the grating-coupling case, the sensor surface may be integral with the grating element, e.g., be one face of a glass or plastic plate with the grating formed on the opposite face or be a part of the grating. As in the prism case, the sensor element may also be a separate element in optical contact with a grating element.

The sensor element may alternatively be integral with a surface providing optical coupling via refraction or diffraction, such as, for example, be one face of a glass or plastic plate with micro-prisms or Fresnel lenses formed on the opposite face, e.g,. as described in WO 92/05426 (the entire disclosure of which is incorporated by reference herein).

With reference to variant (i) above, controlled variation of the beam cross-section may be obtained by "oblique incidence" of the beam at the entrance surface of an ATR-body. By "oblique incidence" is meant that the angle scan only includes angles on one and the same side of the normal to the entrance surface. In this way, the diameter in the plane of incidence of the beam passing through the prism onto the sensor surface will vary during the angle scan so that it is largest for the smallest angle of incidence at the internally reflective surface of the ATR-body, and smallest for the largest angle of incidence, thereby giving a reduced variation of the illuminated area and reducing the dependence of the length of the illuminated area on the sensor surface with the angle of incidence.

While the oblique incidence at the ATR-body, on the one hand, thus will provide for an at least substantially reduced variation of the irradiance of the illuminated area of the sensor surface, such oblique incidence may, on the other hand, give rise to beam walking (as defined above).

For scanner mirrors with symmetric scan mirror angle-amplitudes used with oblique incidence to minimize variation of irradiance, beam walking may be avoided by having the collimated beam pass of a wedge shaped transparent body before reaching the ATR-body to thereby obtain a fixed illuminated area center.

An orthogonal incidence of the beam at the entrance surface of the ATR-body, as in the prior art system disclosed in the above-mentioned WO 98/34098, and symmetric scan mirror amplitudes also provides a symmetric angle of incidence range (i e., symmetric angle of incidence amplitude around the center angle of incidence corresponding to the center angles of the scanner mirrors), e.g., 70.0±6.0°. However, in an optical design based on "oblique incidence" of the beam at the entrance surface of the ATR-body, and a wedge-shaped transparent body to eliminate beam walking, the angle of incidence amplitudes will be non-symmetric, e.g., ranging from 70.0+7.0° to 70.0−6.0°.

Alternatively, beam walking of the collimated beam caused by the irradiation variation minimizing the oblique incidence surface on the ATR-body may be eliminated by using asymmetric scan-mirror angle amplitudes, the asymmetry of the scan-mirror amplitudes providing the desired fixed illuminated area center.

In one embodiment, the scanner mirrors comprise first and second oscillating mirrors, the angle scan amplitudes of which are symmetrical around the center angle of the scanning, which center angle corresponds to the operational center angle of incidence range of the collimated beam. Preferably, the scan angle amplitude ratio of the second oscillating mirror to that of the first oscillating mirror is from about 1 to about 10.

In another embodiment, the scanner mirrors comprise first and second rotating mirrors. Preferably, the scan angle amplitude ratio of the second rotating mirror to that of the first rotating mirror is from about 1 to about 10.

As to variant (ii) above, the power of the light beam produced by the light source, i.e., the light output, may be controlled by regulating the drive current/voltage of the light source, and more particularly to increase the drive current/voltage as the angle of incidence at the sensor surface is increased. Alternatively, the light beam may be caused to pass an electromechanical beam intensity attenuator, such as a filter means having an electronically controlled variable attenuating effect on the light intensity of the beam, e.g., a linear polarizer rotated in relation to a following p-polarizer, or variable neutral density filters. Such filter means may be arranged in the path of either (or possibly both of) the incident or the reflected light beam, preferably before the incident light beam is reflected by the scanning means. When regulating the light source drive current or voltage, or the drive current or voltage for the beam intensity attenuator, a control signal from the photodetector, where the control signal is proportional to the detected irradiance on the detector, can be used in the regulating process.

According to variant (iii) mentioned above, a combination of variants (i) and (ii) may be used. For example, it may be found convenient to use variant (i) for a first range of incident angles, and variant (ii) for a second range of incident angles.

While usually a single light source (e.g., a light emitting diode, or a laser diode) together with a lens system is used to create the collimated beam, the use of a plurality of light sources may also be contemplated to create a plurality of collimated beams to be scanned in parallel by the scanning means. In this way, a plurality of parallel sensor surfaces may be illuminated and sensed. It is, of course, also possible to use two or more light sources to create a combined single beam. These light sources may have identical wavelength or different wavelengths.

As already mentioned, the inventive concept of the present invention as described above, is also applicable to other TIR-based technologies than ATR-spectroscopy. Thus, for instance, rather than measuring the intensity of a totally internally reflected beam of light, fluorescence or phosphorescence emitted from a sensing surface due to excitation by evanescent wave resulting from the total internal reflection may be measured versus angle of incidence. Such fluorescence or phosphorescence may be emitted from either natively fluorescent of phosphorescent sample molecules or molecules labeled with a fluorophore or phosphorophore. Total internal reflection fluorescence is commonly referred to as TIRF.

In SPR-TIRF or SPR-total internal reflection phosphorescence, an SPR-field is used to stimulate the emission of fluorescence or phosphorescence.

Alternatively, light originating from evanescent wave excited scattering at the sensing surface may be measured versus angle of incidence. This technology is usually referred to as STIR (scattered total internal reflection).

The use of TIRF, total internal reflection phosphorescence and STIR, respectively, is described in, for example, U.S. Pat. No. 5,313,264.

It is also possible to use any one of the above non-ATR techniques in combination with ATR, i.e., in combination with measuring the intensity of a totally internally reflected light beam.

U.S. Pat. No. 6,194,223, for example, discloses a method for detecting an analyte, wherein a first signal from SPR-measurement and a second signal from fluorescence measurement are independently analyzed.

WO 98/22808 discloses an SPR apparatus comprising a first detector for detecting light internally reflected from a sensor surface, and a second detector for detecting light scattered or emitted from an analyte bound at the sensor surface.

The entire disclosures of the three patent publications mentioned above are incorporated by reference herein.

In the following the invention will be described, by way of example only, with regard to some specific embodiments thereof.

Figure 2:
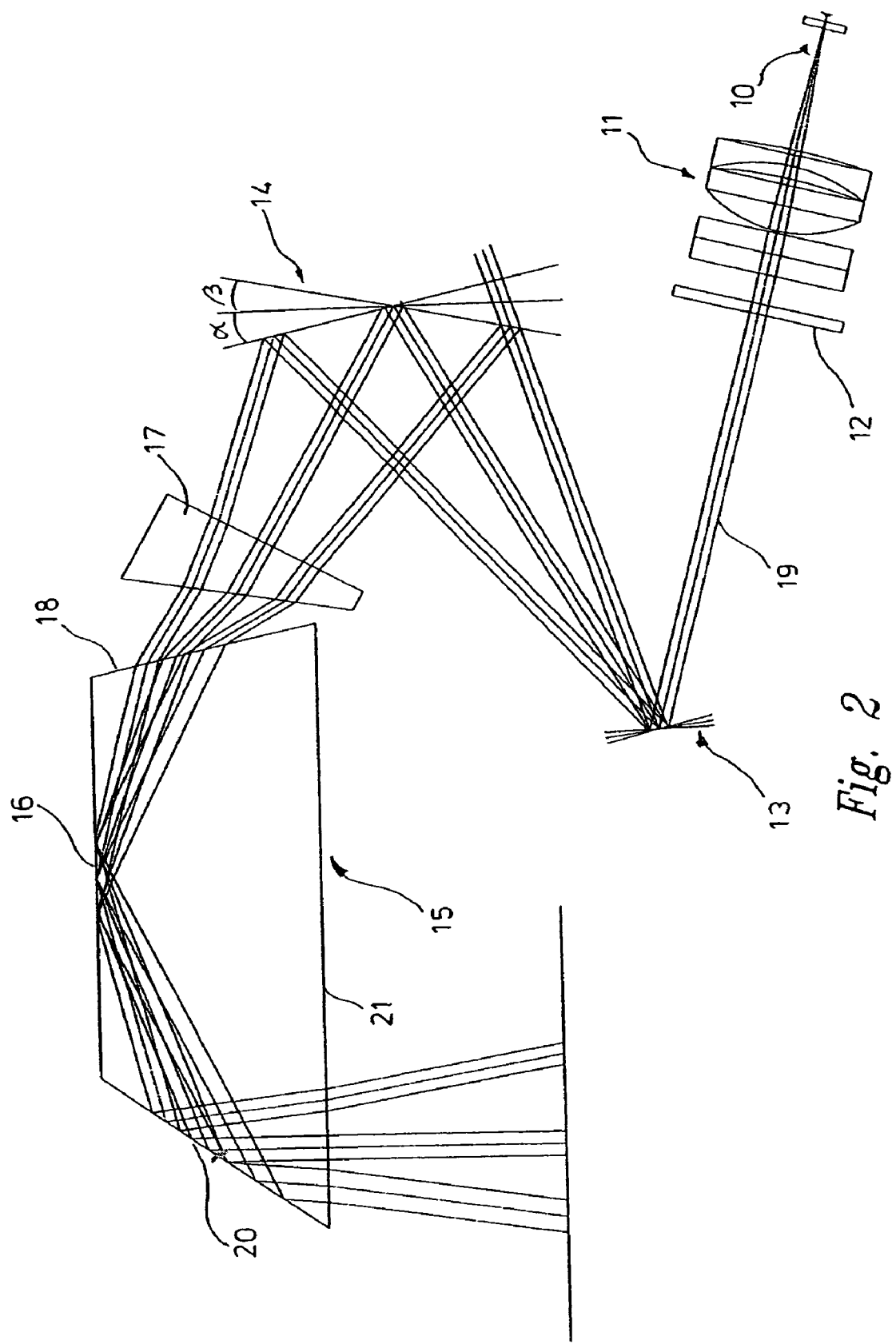
FIG. 2 is a schematic sectional view of an embodiment of apparatus according to the present invention.

The invention may advantageously be applied to a TIR-based optical system of the general type disclosed in the above-mentioned WO 98/34098 and schematically illustrated in FIG. 1 as briefly described above. FIG. 2 discloses a modification according to the present invention of a part of the prior art system illustrated in FIG. 1. Like the system in FIG. 1, the inventive embodiment of FIG. 2 comprises a light source 10, e.g., a light emitting diode (LED), collimator optics 11, an interference filter 12, a pair of scanning mirrors, namely a first scanning mirror 13 and a second scanning mirror 14, and an ATR-prism 15 with a sensor surface 16. The two scanning mirrors 13 and 14 are arranged to have symmetric scan-mirror angle amplitudes as is shown in FIG. 2 (α=β). Such scanning mirrors are well known in the art, and exemplary systems are described in the above-mentioned WO 98/34098.

The sensor surface 16 may, as is well known in the art, be applied directly on the prism 15 or be provided on a separate element, as described in, for example, EP-B-442922, which element is light-coupled to the prism via an immersion oil or a so-called optointerface as described in, for example, U.S. Pat. No. 5,164,589. The sensor surface per se may be any of a variety of sensor surfaces and will not be described herein any further. Suffice it to say that exemplary sensor surfaces are described in U.S. Pat. No. 5,242,828 and U.S. Pat. No. 5,436,161. (The disclosures of the above-mentioned U.S. and European patents are incorporated by reference herein).

In contrast to the prior art system, the optical system of FIG. 2 additionally comprises a wedge-shaped prism 17 inserted between the second scanning mirror 14 and the ATR-prism 15. Also, in the embodiment in FIG. 2, the entrance surface 18 on the ATR-prism 15 for the incident light is inclined in relation to the incident light beam such that the angle of incidence will be oblique over the whole scanned angular range as will be described below.

A beam of collimated light 19 from the light source 10 and collimated optics 11 is reflected by the scanning mirrors 13, 14 via wedge prism 17 into prism 15 where the beam is totally internally reflected at the sensor surface 16. The reflected light is then, in the illustrated case, totally internally reflected at plane prism side 20 to leave the prism through plane prism side 21 parallel to the sensor surface. The reflected light may then, in the same way as in FIG. 1 (but not shown in FIG. 2), pass a polarizer and an objective to produce an image on a detector array. For further details on the beam path components following after the prism 15, as well as on the light source and collimator optics, it is referred to the above-mentioned WO 98/34098. It may be noted that it is advantageous to focus part of the light reflected at an area of the sensor surface without sensing function, and/or light reflected at the coupling prism onto a separate part of the detector array or separate detector to determine the momentary incident angle (or wavelength).

In FIG. 2, the collimated beam enters the prism 15 with an oblique incidence angle, which means that all beams during the angle scan impinge on the prism obliquely or, expressed in another way, are all on one and the same side of the normal to the inclined entrance side 18 of prism 15, as opposed to the situation in the prior art system in FIG. 1, where the center beam impinges orthogonally to the entrance side of the prism.

The oblique incidence in FIG. 2 causes, as is readily appreciated, the length of the intersection area of the beam with the inclined prism entrance surface 18 (length L=[beam diameter(angle)]/cosine(angle)) to be continually decreased as the angle of incidence at the sensor surface 16 is increased, and thereby the length of the illuminated sensor surface area of fixed center position, is kept mainly constant. In other words, the width of the beam incident at the sensor surface 16 (in the plane of incidence) will vary during the angle scan so that it is largest for the smallest angle of incidence at the sensor surface and smallest for the largest angle of incidence at the sensor surface. The oblique beam entrance into the prism will thus counteract the dependence of the length of the intersection area (and thereby the illuminated sensor surface area) on the cosine(angle)$^{-1}$ and provide a substantially constant illuminated area and irradiance on the sensor surface during the angle scan.

It is appreciated that when using scan mirrors with symmetric scan angle amplitudes as illustrated in FIG. 2 in combination with an oblique beam entrance onto the ATR-prism to maintain a substantially constant beam intersection area with the sensor surface according to the present invention, the oblique beam incidence may cause beam walking, i.e., a moving center of the illuminated area. This is, however, obviated by wedge prism 17 which has a geometry and position selected to counteract the asymmetry in the angle scan caused by the oblique beam entrance into the prism and produce a symmetric angle scan. The appropriate wedge geometry, including angle of entrance, thickness and angle of exit, to obtain such a fixed illuminated area center and eliminate beam walking may readily be selected by the skilled person in each particular situation, bearing in mind that the use of wedge prisms (anamorphic prisms) in optical systems is per se known in the prior art.

For instance, beam shaping based on anamorphic prisms is described in, for example, O'shea, Donald C., "Elements of Modern Optical Design", Wiley & Sons, Inc. 1985, pages 259–262; and Marshall, Gerald F., "Laser Beam Scanning", Marcel Dekker, Inc. 1985, pages 346–349. A prism couple is mounted in a fixed (non-scanned) collimated beam with the purpose of obtaining a collimated beam of new cross-section ratio, the changed beam also being fixed and parallel with the first beam. An example hereof is the transformation of the elliptical output of a diode laser into a circular beam, such as e.g., in commercial collimation laser pens.

Also, beam scanning based on wedge prisms is described in Marshall, Gerald F., "Scanning Devices and Systems", Applied Optics and Optical Engineering vol. vi, Academic Press Inc, 1980, pages 248–250. A collimated beam incident onto a prism is rotated about an axis collinear with the incident beam for the purpose of refracting this beam and creating a spatial cone in space formed by the swept refracted emergent collimated beam. Further, it is described how, by the same principle, two wedge prisms contra-rotating in tandem can be used to create an elliptical cone of a swept beam position on a screen. (The entire contents of the above two publications are incorporated by reference herein.)

A main advantage of symmetric mirror scan angle-amplitudes is the resulting approximately identical angle of incidence vs. time relationship, which provides a distribution of measured angle(time)-data symmetrical around the scan angle center, which in turn improves the speed and accuracy of the computed SPR-angle vs. time data. Another advantage of symmetric scan angle-amplitudes is a less complex driver electronics for the two synchronized mirror scanners as well as less wear of the scanner bearing design, i.e., less torsional stress, due to a symmetrical torsional (turning) moment.

Figure 3:
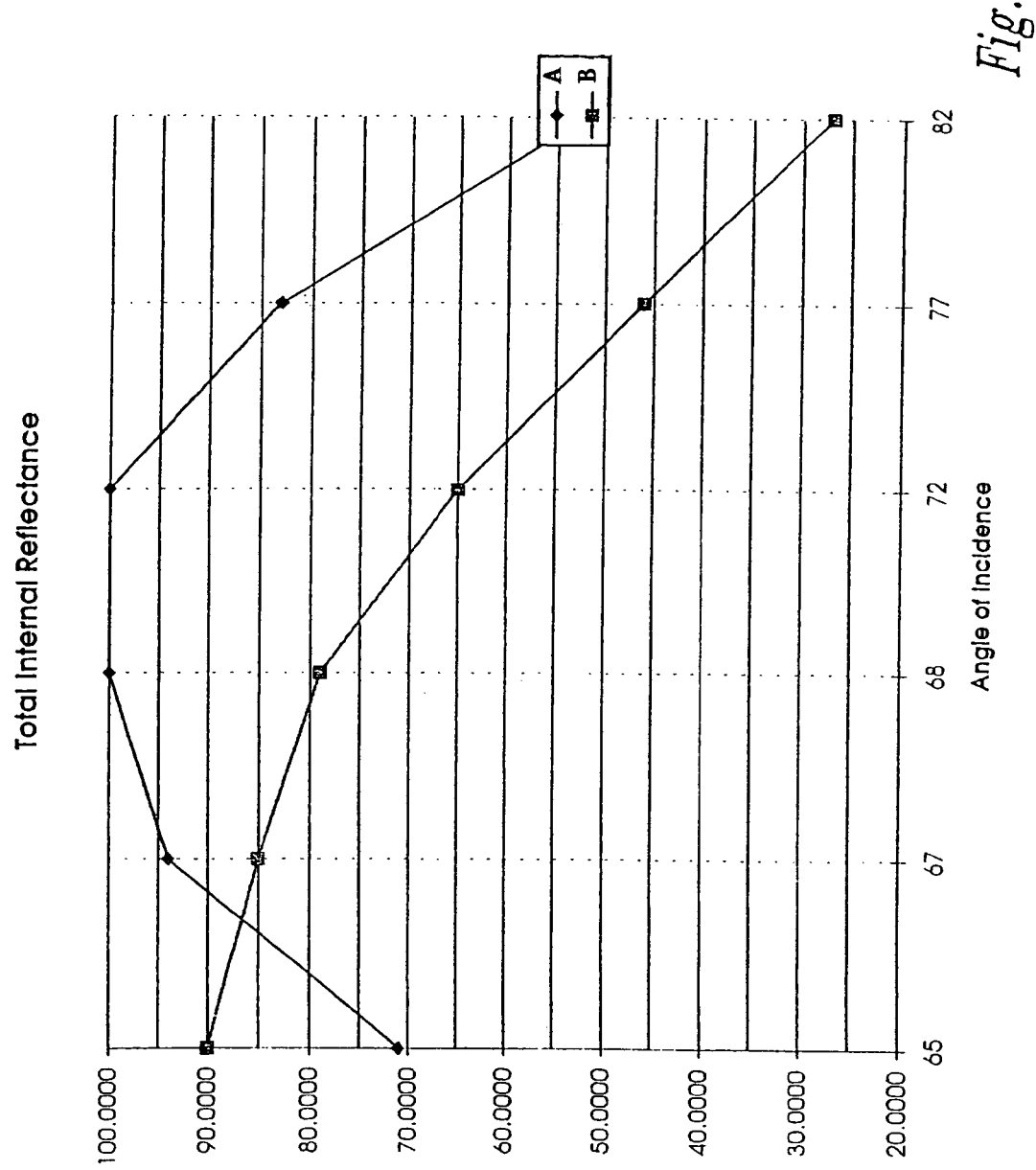
FIG. 3 is a diagram showing total internal reflectance (TIR) versus incident angle for (A) the apparatus of FIG. 2, and (B) a prior art ATR-sensor with fixed center during angle scan.

FIG. 3 shows the variation of the reflectance versus incident angle for an optical set-up according to FIG. 2 (curve A) as compared with that for a prior art set-up with orthogonal incidence and symmetric scan angle amplitudes (curve B). As demonstrated by FIG. 3, the embodiment of FIG. 2 causes the dependence of the reflectance on the incident angle to have a maximum reflectance within a more or less symmetrical curve shape (A) rather than the monotone sloping curve (B) obtained in the prior art. It is appreciated by the skilled person that by the use of a suitable computer software algorithm, measurement data obtained with the apparatus in FIG. 2 may be adjusted for this substantially reduced and controlled variation of the reflectance during the angle scan.

As mentioned above, computer software algorithms have been used in the prior art to normalize the TIR curve in SPR biosensor instruments. For the commercial BIACORE® instruments referred to above (i.e., static optical configuration), such a normalization procedure includes:

a) Filtering of measured reflectance data vs. time at each angle within the simultaneous angle of incidence range in order to obtain a continuous TIR-data curve (total reflectance vs. angle curve or plot). Such averaging over time of the detector response signal reduces the temporal scatter/noise in the TIR-data. The less scattered data, the faster is the filtering data processing (calculations) thereof into a curve smooth enough for high accuracy detection of dips and peaks.

b) Curve fitting an analytical curve to the filtered TIR-curve. The less complex curve shape, the faster, less complex, and more accurate curve fitting data processing (calculation).

c) Normalization, calculation of correction data for the analytical TIR-data curve fit. The correction-correction data-matrix is stored in a computer memory, and is added to the analytical TIR-data curve to provide a normalized analytical TIR-data (as constant total internal reflectance as possible as function of angle of incidence).

When the sample is added and bound to the SPR-sensor surface, it causes a minimum in the measured TIR-curve, the resonance curve. The resonance curve's reflectance data are filtered in real-time and the data-data matrix is added. In a real-time computer process, an analytical curve is fitted to this normalized SPR-curve, and the curve's angular position is calculated in real-time. A normalized TIR-curve improves the measurement accuracy of the angle position of the SPR-reflectance dip (or converted to reflectance peak). If no normalization is done, the slope and low spatial frequency scatter/noise in the TIR-data will disturb the curve-shape of the SPR-curve and limit the accuracy of measured absolute and changes in SPR-curve shape parameters (reflectance minimum/minima, reflectance peak/peaks, curve-dip/peak width) or SPR-angles, and of SPR-angle vs. time kinetic measurements.

It is appreciated that such software may be improved to also adjust for the variation of the reflectance during the angle scan as obtained with the embodiment in FIG. 2.

Figure 4:
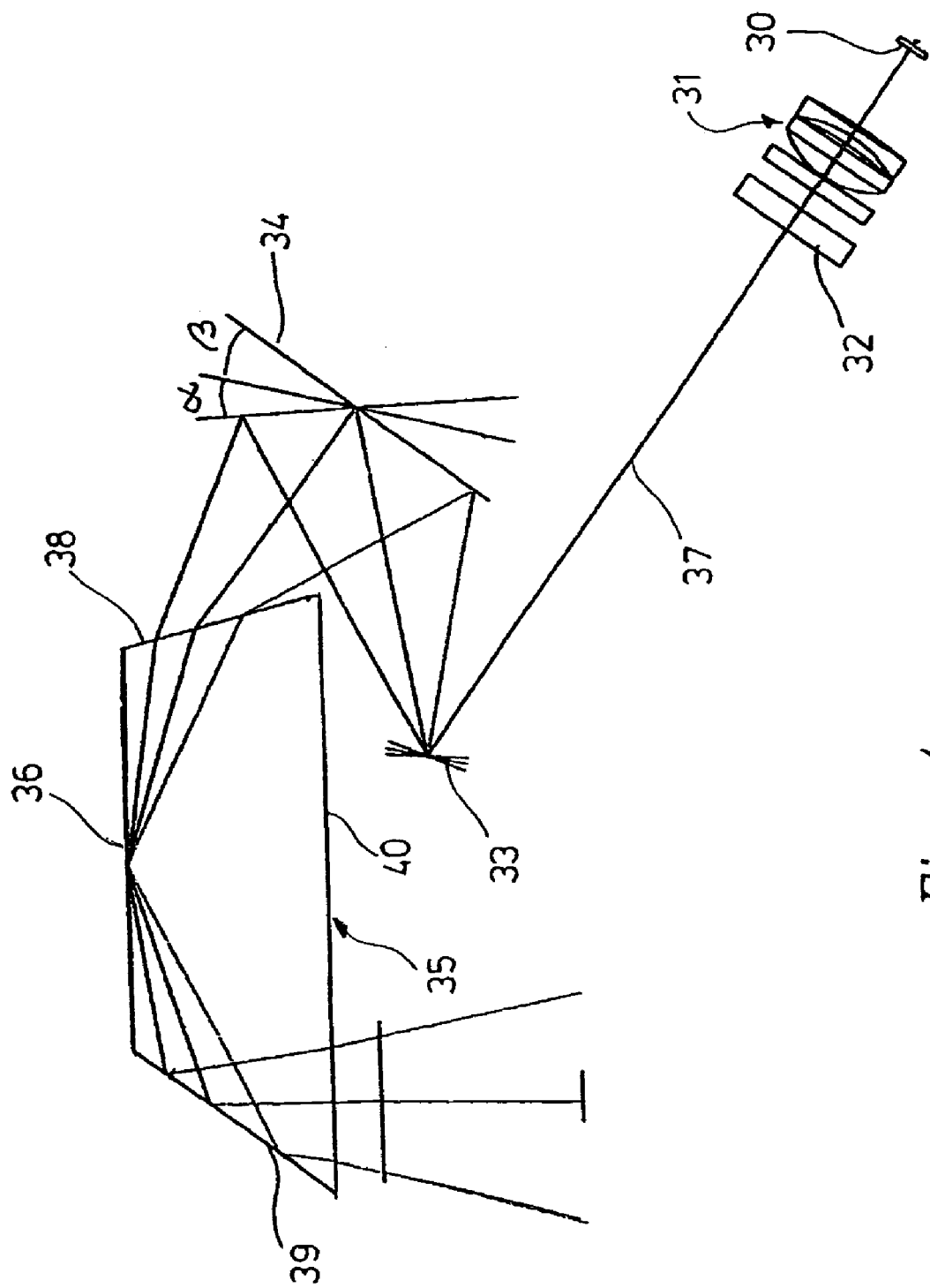
FIG. 4 is a schematic sectional view of another embodiment of apparatus according to the present invention.

An alternative embodiment of the present invention is shown in FIG. 4. Like the embodiment in FIG. 2, it comprises a light source 30, collimator optics 31, an interference filter 32, a first scanning mirror 33, a second scanning mirror 34, and an ATR-prism 35 with a sensing surface 36. Also, in conformity with the embodiment in FIG. 2, a collimated light beam 37 from the light source 30 and collimator optics 31 is reflected by the scanning mirrors 33, 34 to impinge at an oblique incident angle at the entrance surface 38 of the prism 35 to thereby counteract variation of the illuminated area of the sensor surface 36 during the angle scan.

In the embodiment of FIG. 4, however, in order to eliminate beam walking, a fixed illuminated area center is ensured by the scan-mirror angle amplitudes being asymmetric (as indicated in the Figure: $\alpha \neq \beta$) in a way that counteracts the asymmetry caused by the oblique incidence at the ATR-prism. This asymmetry of the scan-mirror angle amplitudes thus replaces the wedge prism 17 in FIG. 2. Techniques for asymmetric scan-mirror angle amplitudes are known per se in the art.

As in the embodiment of FIG. 2, the beam totally reflected at the sensing surface 36 is then reflected at plane prism side 39 and exits the prism 35 through prism side 40 to be imaged on a detector array.

Figure 5:
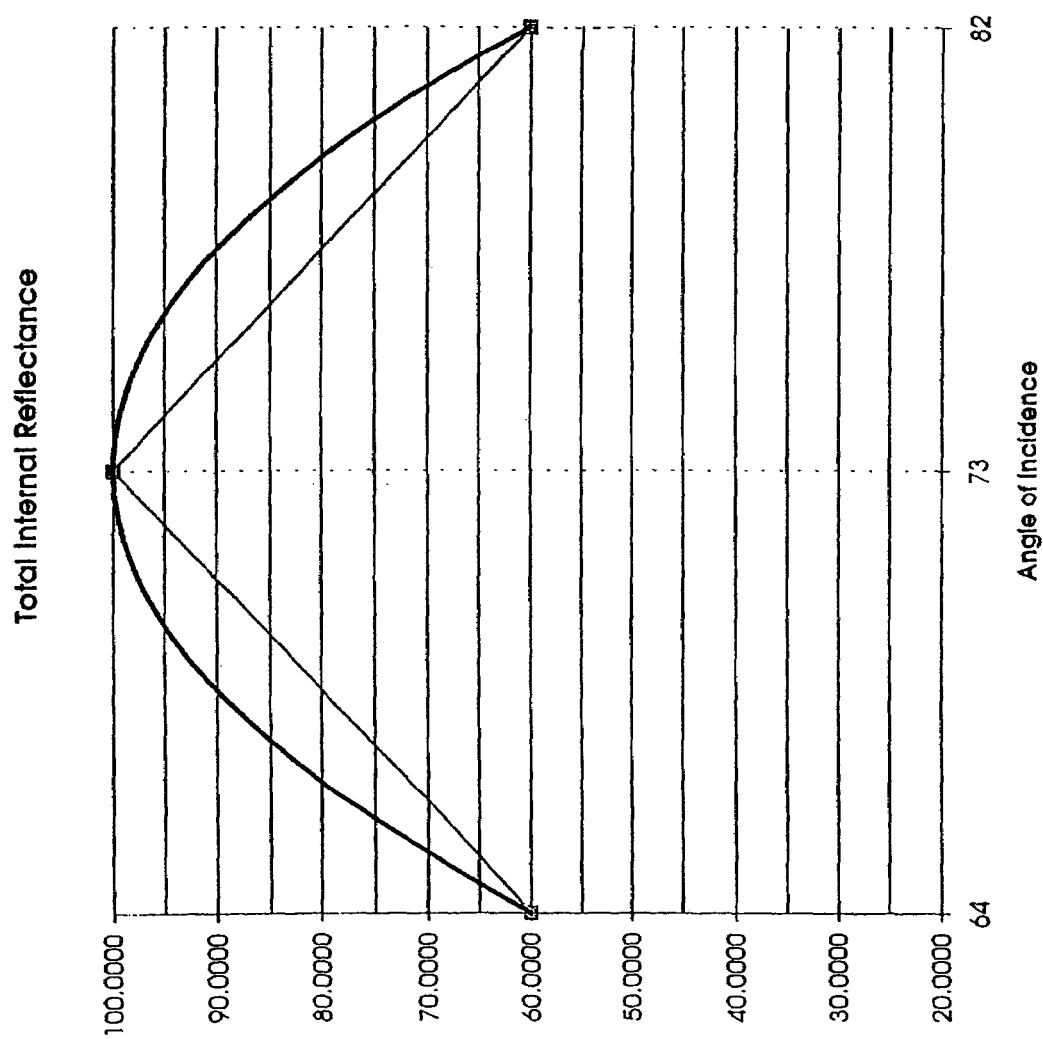
FIG. 5 is a diagram showing total internal reflectance (TIR) versus incident angle during angle scan for the apparatus of FIG. 4.

The TIR-curve obtained with the embodiment in FIG. 4 is illustrated by the diagram of FIG. 5. In the same way as for the TIR-curve obtained for the embodiment in FIG. 4, the TIR-curve in FIG. 5 may be normalized by a suitable computer software algorithm.

From the foregoing, it will be appreciated that, although specific embodiments of this invention have been described herein for purposes of illustration, various modifications may be made without departing from the spirit and scope of invention. Accordingly, the invention is not limited except by the appended claims.

What is claimed is:

1. An optical sensor system, comprising:
 a sensor unit having a planar sensing surface,
 means for illuminating an area of the sensing surface with a collimated beam of electromagnetic radiation,
 means for scanning the incident electromagnetic radiation over a range of incident angles,
 means for imaging electromagnetic radiation exiting the sensing surface onto a detector means, and
 means for varying the cross-sectional intensity of the collimated beam of electromagnetic radiation incident onto the sensing surface to maintain a substantially constant irradiance of the illuminated sensing surface area over the scanned range of incident angles.

2. The sensor system according to claim 1, wherein the means for varying the cross-sectional intensity of the beam of collimated electromagnetic radiation comprise means for varying the cross-sectional area's length of the beam in the plane of incidence on the sensing surface.

3. The sensor system according to claim 1, wherein the means for varying the cross-sectional intensity of the beam of collimated electromagnetic radiation comprise means for varying the radiation power of the beam.

4. The sensor system according to claim 1, wherein the collimated beam of electromagnetic radiation is internally reflected at the sensing surface.

5. The sensor system according to claim 4, wherein the detector means comprise means for detecting radiation internally reflected from the illuminated sensing surface.

6. The sensor system according to claim 4, wherein the detector means comprise means for detecting radiation originating from evanescent wave stimulated fluorescence or phosphorescence.

7. The sensor system according to claim 4, wherein the detector means comprise means for detecting radiation originating from evanescent wave stimulated scattering.

8. The sensor system according to claim 1, wherein the sensing surface comprises a layer of a metal supporting surface plasmon resonance (SPR).

9. The sensor system according to claim 1, wherein the sensing surface comprises a plurality of discrete sensing zones.

10. An optical sensor system, comprising:
a sensor unit having a planar sensing surface,
means for illuminating an area of the sensing surface with a collimated beam of electromagnetic radiation to be reflected at the surface,
means for scanning the incident electromagnetic radiation over a range of incident angles,
means for imaging electromagnetic radiation reflected from the sensing surface onto a detector means, and
means for varying the cross-sectional intensity of the beam of electromagnetic radiation reflected from the sensing surface and imaged onto the detector means to counteract the effect on the reflected beam of any deviation from a substantially constant irradiance of the illuminated sensing surface over the scanned range of incident angles.

11. The sensor system according to claim 10, wherein the means for varying the cross-sectional intensity of the reflected beam of electromagnetic radiation comprise a beam power attenuator for varying the radiation power of the beam.

12. The sensor system according to claim 11, wherein the beam power attenuator is an electro-mechanical beam power attenuator.

13. The sensor system according to claim 11, wherein the beam power attenuator is selected from co-operating linear polarizers and variable density filters.

14. The sensor system according to claim 10, wherein the collimated beam of electromagnetic radiation is internally reflected at the sensing surface.

15. The sensor system according to claim 10, wherein the sensing surface comprises a layer of a metal supporting surface plasmon resonance (SPR).

16. The sensor system according to claim 10, wherein the sensing surface comprises a plurality of discrete sensing zones.

* * * * *